Dec. 11, 1951 J. DE VINK Plant Pat. 1,051
ROSE PLANT
Filed June 2, 1950
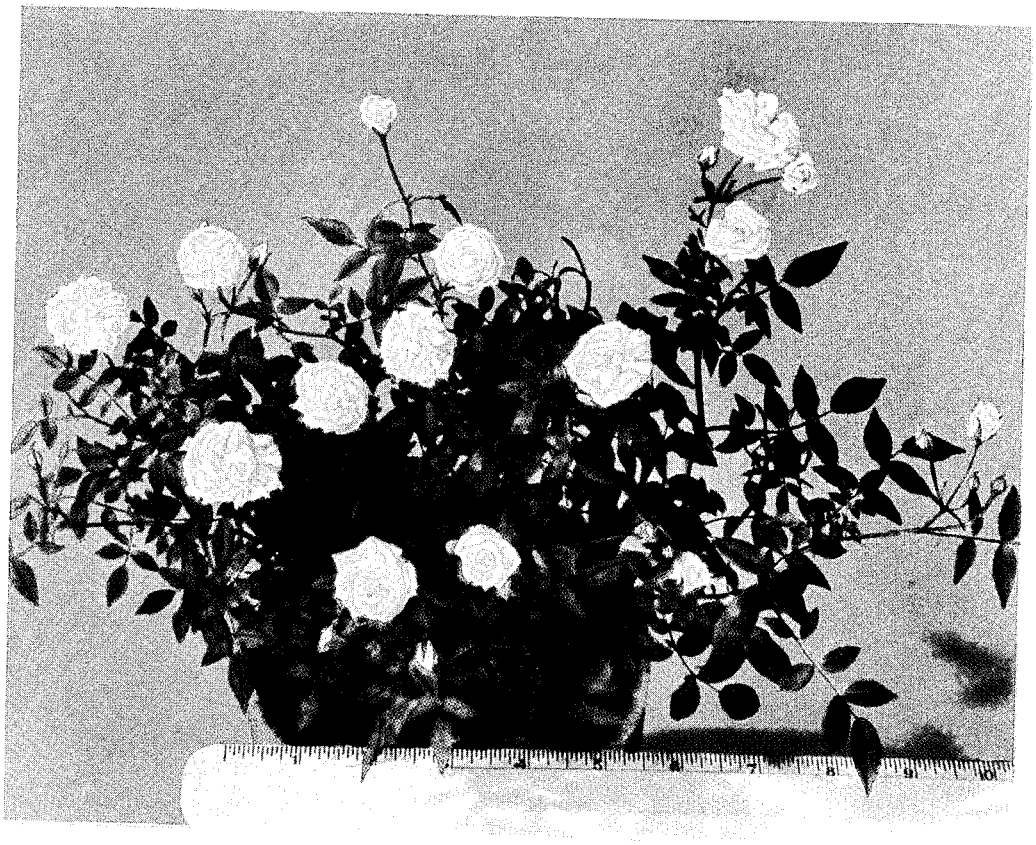
Inventor.
John de Vink
By: Robb & Robb
Attorneys.

Patented Dec. 11, 1951 Plant Pat. 1,051

UNITED STATES PATENT OFFICE 1,051

ROSE PLANT

John de Vink, Boskoop, Netherlands, assignor to The Conard-Pyle Company, West Grove, Pa., a corporation of Pennsylvania Application June 2, 1950, Serial No. 165,694

1 Claim. (Cl. 47—61)

The present invention relates to a new and distinct variety of rose plant of the miniature rose class, originated from crossing the variety "Mlle. Cecile Brunner" (unpatented) × "Tom Thumb" (Plant Patent No. 169).

This new rose variety is characterized by a combination of qualities which make it markedly superior to the white miniature variety "Pixie" (Plant Patent No. 408) which heretofore has attained the highest rating.

The new variety is distinguished from its parents, as well as from other miniature rose varieties, by the following dominant characteristics:

(1) It is wholly without thorns;

(2) It has no anthers or stamens visible under 10-power magnification;

(3) Its foliage is abundant and attractive;

(4) As its first flower petals open, the buds more nearly resemble the opening buds of a hybrid tea rose than does any other miniature rose;

(5) Under favorable conditions, its white flowers show tinges of Pale Flesh color which is deepest towards the center of the flower; and (6) The flower petals are very satiny.

Asexual reproduction of this new variety by budding at Boskoop, Holland, and also by budding and own-rooting at West Grove, Pennsylvania, U. S. A., shows that the foregoing characteristics come true to form and are established and transmitted through succeeding propagations.

The accompanying drawing shows a potted specimen plant of the new variety, in comparison with an inch-marked scale, with the flowers and foliage of the plant depicted in different stages of development.

The following is a detailed description of the new variety, with color terminology in accordance with Ridgway's Color Standards and Nomenclature, except where general color terms of ordinary dictionary significance are used:

Type: Hardy; dwarf; greenhouse; outdoor; seedling; for cut flowers and garden decoration.

Class: Miniature.

Breeding: Seedling.

*Seed parent.*—"Mlle. Cecile Brunner" (unpatented).

*Pollen parent.*—"Tom Thumb" (Plant Patent No. 169).

Propagation: Holds its distinguishing characteristics through succeeding propagations by cuttings and budding.

*Flower*

Locality where grown: West Grove, Pennsylvania.

Flowers borne: Usually singly to stem; on normal, medium length stems.

Quantity of bloom: Free in greenhouse.

Continuity: Intermittent to continuous.

Fragrance: Moderate; spicy.

Bud:

*Peduncle.*—Medium length; medium heavy; bending to erect; green; medium rough; medium number of small, reddish prickles.

*Before calyx breaks.*—Size—small. Form—pointed; ovoid; with foliaceous appendages on the surface of the bud; with medium cut foliaceous parts extending beyond the tip of the bud equal to one-fourth or more of its length.

*As calyx breaks.*—Color—white.

*As first petal opens.*—Size—medium. Form—ovoid to globular. Color—outside: White tinted with Cameo Pink, Plate XXVI; sometimes with small tinges of Thulite Pink, Plate XXVI; inside: White, lightly tinted with Cameo Pink, Plate XXVI; sometimes with tinges of Thulite Pink, Plate XXVI.

*Opening.*—Opens up well; retarded from opening by cold weather.

Bloom:

*Size when fully open.*—Small; 1 inch to 1¼ inches.

*Petalage.*—Very double; from 45 to 60 petals; arranged regularly.

*Form.*—Cupped at first, becoming high centered; petals being at first cupped inward; outer petals becoming later, at maturity, curved outward, with inner petals rather erect or slightly cupped inward.

Petals: Medium thick; with inside satiny and outside shiny.

*Shape.*—Outer—obovate to oval with apex pointed. Intermediate—almost oval with apex pointed. Inner—almost oval with apex pointed.

*Color.*—Petals may have shades of Pale Lumiere Green, Plate XVII, at base point of attachment or along lower part of midrib of outside petals; colors may be modified by being tinted or tinged with shades of pink.

This description of a newly opened flower was made from a rose grown in a greenhouse in the month of November, 1949, at West Grove, Pennsylvania.

*Color.*—Outer petal—outside surface: white; sometimes with a tinge of Rose Color, Plate XII, at apex; inside surface: white; sometimes with a tinge of Rose Color, Plate XII, at apex. Intermediate petal—outside surface: white; inside surface: white. Inner petal—outside surface: white; inside surface: white. Petaloids may show slight tinges of Rose Pink, Plate XII, or Deep Rose Pink, Plate XII, at side edges.

This description was made from a rose that was open for three days in a greenhouse in the month of November, 1949, at West Grove, Pennsylvania:

*Color.*—Outer petal—ouside surface: white; sometimes with light tints of Deep Rose Pink, Plate XII, near apex; inside surface: white; sometimes with light tints of Deep Rose Pink, Plate XII, near apex. Inner petal—outside surface—white; sometimes with tints of Rose Pink, Plate XII, at very edges; inside surface—white; sometimes with tints of Rose Pink, Plate XII, at very edges.

*General color effect.*—Newly opened flower—white; sometimes with very slight tinges of Rose Color, Plate XII, at apexes of outermost petals. Three days open—white; occasionally with tints of Rose Pink, Plate XII.

*Behavior.*—Persist; fading brown; affected by cold weather, not opening fully. Under conditions of cool and/or humid atmosphere and lower light intensity, a glow or shading of Pale Flesh Color, Plate XIV, to Shrimp Pink, Plate I, may appear in the flower. This glow deepens toward the center of the flower and fades toward the outer edges.

*Flower longevity.*—On bush in greenhouse—9 days in November. Cut roses grown in greenhouse kept at living room temperatures—3 to 4 days in November.

*Reproductive organs*

Stamens: None found at 10-power magnification.
Filaments: None found at 10-power magnification.
Anthers: None found at 10-power magnification.
Pollen: None.
Pistils: Many.

Styles: Uneven; most medium length; medium heavy; bunched.
Stigma: White.
Ovaries: Most enclosed in calyx.
Hips: None found.
Sepals: Permanent; medium length; spear-shaped.
Seeds: None found.

*Plant*

Foliage:

*Leaves.*—Compound of seven leaflets; abundant; small; moderately heavy.

*Leaflets.*—Shape—ovoid to lanceolate with apex acute; base round to acute; margin simply serrate.

*Color.*—*Mature*—upper surface—Dark Dull Yellow-Green, Plate XXXII; under surface—Light Elm Green, Plate XVII. *Young*—upper surface—Cerro Green, Plate V; under surface—Light Cress Green, Plate XXXI.

*Rachis.*—Medium heavy. Upper side—grooved. Under side—sparsely thorny.

*Stipules.*—Medium length; medium width; with medium length points turning out at an angle of less than 90°.

*Disease.*—Resistant to blackspot.

Growth:

*Habit.*—Upright; branched.

*Growth.*—Free; average overall height 8 inches.

*Canes.*—Medium heavy.

*Main stems.*—Color—green. Thorns, prickles, and hairs—none.

*Branches.*—Color—green. Thorns, prickles, and hairs—none.

*New shoots.*—Color—green. Thorns, prickles, and hairs—none.

I claim:

A new and distinct variety of rose plant of the miniature rose class, characterized as to novelty by its thornless habit of growth, by the absence of anthers or stamens, by its abundance of attractive foliage, by the resemblance of its buds as the first petals open to the opening buds of a hybrid tea rose, and by the satiny and white color of its flowers showing tinges of pale flesh color deepening towards the center of the flowers, substantially as shown and described.

JOHN DE VINK.

No references cited.